(12) United States Patent
Lynn et al.

(10) Patent No.: US 8,315,890 B2
(45) Date of Patent: *Nov. 20, 2012

(54) SYSTEM AND METHOD FOR GROUPING CLAIM RECORDS ASSOCIATED WITH A PROCEDURE

(75) Inventors: Thomas E. Lynn, Chapel Hill, NC (US); Thinzar Mra Nyun, Sudbury, MA (US); Lynn Anne Richards, Brooklyn Park, MN (US); Kimberly Sanborn, Sutton, MA (US)

(73) Assignee: OptumInsight, Inc., Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/885,995

(22) Filed: Sep. 20, 2010

(65) Prior Publication Data

US 2011/0010368 A1 Jan. 13, 2011

Related U.S. Application Data

(63) Continuation of application No. 11/759,616, filed on Jun. 7, 2007, now Pat. No. 7,801,749.

(51) Int. Cl.
G06Q 40/00 (2012.01)
(52) U.S. Cl. ..................... 705/4; 705/2; 705/3
(58) Field of Classification Search ............ 705/2, 3, 705/4
See application file for complete search history.

(56) References Cited

U.S. PATENT DOCUMENTS

| | | | |
|---|---|---|---|
| 4,667,292 A | 5/1987 | Mohlenbrock et al. | |
| 5,557,514 A | 9/1996 | Seare et al. | |
| 5,835,897 A * | 11/1998 | Dang | 705/2 |
| 5,970,463 A | 10/1999 | Cave et al. | |
| 6,370,511 B1 | 4/2002 | Dang | |
| 6,393,404 B2 | 5/2002 | Waters et al. | |
| 7,389,245 B1 * | 6/2008 | Ashford et al. | 705/2 |
| 2005/0240447 A1 * | 10/2005 | Kil et al. | 705/4 |
| 2005/0278196 A1 * | 12/2005 | Potarazu et al. | 705/2 |
| 2007/0106533 A1 * | 5/2007 | Greene | 705/2 |

OTHER PUBLICATIONS

U.S. Appl. No. 11/369,198, filed Mar. 6, 2006.

(Continued)

Primary Examiner — Elizabeth Rosen
(74) Attorney, Agent, or Firm — Bridget M. Hayden; Dorsey & Whitney LLP

(57) ABSTRACT

A system and computer-implemented method for grouping medical records implements a multi-level analysis of the records. The level of analysis for each record is determined based upon the time proximity of each record to the defining medical procedure or service (anchor procedure) to be analyzed. Once an anchor procedure is identified, claim records are processed to determine whether any of the records should be grouped with the anchor procedure into a procedure episode group (PEG). First, the date of service for each claim record is identified to determine whether the claim record falls within time window. The claim records falling within the window then are assessed to determine whether each claim record is sufficiently related to the anchor procedure (for example, by determining whether the diagnostic, procedure, or episode treatment group coding of each claim record is associated with the anchor procedure). The requisite level of relationship between the claim records and the anchor procedure depends upon the position of the records within the time window. Only those claim records having the requisite relationship level associated with the portion of the time window in which they fall are included in the PEG.

8 Claims, 15 Drawing Sheets

OTHER PUBLICATIONS

Episode Risk Groups™ Nears 45 Million Covered Lives; AetnaUSQA and Conventry Health Care License ETGs and ERGs PR Newswire, May 20, 2002, p. 1.

Europe Search Report dated Oct. 9, 2008, for application No. EP08251982.8.

"Highmark Licenses Symmetry's Episode Risk Groups™," PR Newswire, Nov. 7, 2002, p. 1.

* cited by examiner

| Claim # | Date | Procedure Code/ Modifier | Provider/ Specialty | ETG | Cost | PEG-Anchor Category | Anchor Flag |
|---|---|---|---|---|---|---|---|
| 1 | 1/1 | 33533-91 | Labcore/ Ancillary | 260 | 100 | | |
| 2 | 1/1 | 99212 | Smith/ FP | 260 | 120 | | |
| 3 | 1/1 | 33533 | Jones/ CV Surgeon | 260 | 6500 | | |
| 4 | 1/1 | 33533 | Jones/ CV Surgeon | 260 | 200 | | |
| 5 | 1/1 | 33533 | Thomas/ CV Surgeon | 260 | 1000 | | |
| 6 | 1/1 | 33533/ AA | Jacobs/ Anesthesia | 260 | 5300 | | |
| 7 | 1/1 | 27130 | Buss/ Orthopedics | 727 | 2300 | | |
| 8 | 1/1 | 33533 | Smith/ FP | 997 | 120 | | |
| 9 | 1/1 | 93682/ AA | Jacobs/ Anesthesia | 260 | 1000 | | |
| 10 | 1/1 | 92982 | Breaker/ Cardiology | 260 | 1500 | | |

Fig. 2A

| Claim # | Date | Procedure Code/ Modifier | Provider/ Specialty | ETG | Cost | PEG-Anchor Category | Anchor Flag |
|---|---|---|---|---|---|---|---|
| 1 | 1/1 | 33533-91 | Labcore/ Ancillary | 260 | 100 | | |
| 2 | 1/1 | 99212 | Smith/ FP | 260 | 120 | | |
| 3 | 1/1 | 33533 | Jones/ CV Surgeon | 260 | 6500 | CABG | |
| 4 | 1/1 | 33533 | Jones/ CV Surgeon | 260 | 200 | CABG | |
| 5 | 1/1 | 33533 | Thomas/ CV Surgeon | 260 | 1000 | CABG | |
| 6 | 1/1 | 33533/ AA | Jacobs/ Anesthesia | 260 | 5300 | | |
| 7 | 1/1 | 27130 | Buss/ Orthopedics | 727 | 2300 | HIPREP | |
| 8 | 1/1 | 33533 | Smith/ FP | 997 | 120 | CABG | |
| 9 | 1/1 | 93682/ AA | Jacobs/ Anesthesia | 260 | 1000 | | |
| 10 | 1/1 | 92982 | Breaker/ Cardiology | 260 | 1500 | TXCAT1 | |

Fig. 2B

| Claim # | Date | Procedure Code/ Modifier | Provider/ Specialty | ETG | Cost | PEG- Anchor Category | Anchor Flag |
|---|---|---|---|---|---|---|---|
| 3 | 1/1 | 33533 | Jones/ CV Surgeon | 260 | 6500 | CABG | |
| 4 | 1/1 | 33533 | Jones/ CV Surgeon | 260 | 200 | CABG | |
| 5 | 1/1 | 33533 | Thomas/ CV Surgeon | 260 | 1000 | CABG | |
| 7 | 1/1 | 27130 | Buss/ Orthopedics | 727 | 2300 | HIPREP | |
| 8 | 1/1 | 33533 | Smith/ FP | 997 | 120 | CABG | |
| 10 | 1/1 | 92982 | Breaker/ Cardiology | 260 | 1500 | TXCAT1 | |

Fig. 2C

| Claim # | Date | Procedure Code/ Modifier | Provider/ Specialty | ETG | Cost | PEG- Anchor Category | Anchor Flag |
|---|---|---|---|---|---|---|---|
| 3 | 1/1 | 33533 | Jones/ CV Surgeon | 260 | 6500 | CABG | |
| 4 | 1/1 | 33533 | Jones/ CV Surgeon | 260 | 200 | CABG | |
| 5 | 1/1 | 33533 | Thomas/ CV Surgeon | 260 | 1000 | CABG | |
| 7 | 1/1 | 27130 | Buss/ Orthopedics | 727 | 2300 | HIPREP | |
| 10 | 1/1 | 92982 | Breaker/ Cardiology | 260 | 1500 | TXCAT1 | |

Fig. 2D

| Claim # | Date | Procedure Code/ Modifier | Provider/ Specialty | ETG | Cost | PEG-Anchor Category | Anchor Flag |
|---|---|---|---|---|---|---|---|
| 3 | 1/1 | 33533 | Jones/ CV Surgeon | 260 | 6500 | CABG | |
| 4 | 1/1 | 33533 | Jones/ CV Surgeon | 260 | 200 | CABG | |
| 5 | 1/1 | 33533 | Thomas/ CV Surgeon | 260 | 1000 | CABG | |
| 10 | 1/1 | 92982 | Breaker/ Cardiology | 260 | 1500 | TXCAT1 | |

Fig. 2E

| Claim # | Date | Procedure Code/ Modifier | Provider/ Specialty | ETG | Cost | PEG-Anchor Category | Anchor Flag |
|---|---|---|---|---|---|---|---|
| 3 | 1/1 | 33533 | Jones/ CV Surgeon | 260 | 6500 | CABG | |
| 4 | 1/1 | 33533 | Jones/ CV Surgeon | 260 | 200 | CABG | |
| 5 | 1/1 | 33533 | Thomas/ CV Surgeon | 260 | 1000 | CABG | |

Fig. 2F

| Claim # | Date | Procedure Code/ Modifier | Provider/ Specialty | ETG | Cost | PEG-Anchor Category | Anchor Flag |
|---|---|---|---|---|---|---|---|
| 3 | 1/1 | 33533 | Jones/ CV Surgeon | 260 | 6500 | CABG | |
| 4 | 1/1 | 33533 | Jones/ CV Surgeon | 260 | 200 | CABG | |
| 5 | 1/1 | 33533 | Thomas/ CV Surgeon | 260 | 1000 | CABG | |

Fig. 2G

| Claim # | Date | Procedure Code/ Modifier | Provider/ Specialty | ETG | Cost | PEG-Anchor Category | Anchor Flag |
|---|---|---|---|---|---|---|---|
| 1 | 1/1 | 33533-91 | Labcore/ Ancillary | 260 | 100 | | |
| 2 | 1/1 | 99212 | Smith/ FP | 260 | 120 | | |
| 3 | 1/1 | 33533 | Jones/ CV Surgeon | 260 | 6500 | CABG | X |
| 4 | 1/1 | 33533 | Jones/ CV Surgeon | 260 | 200 | CABG | X |
| 5 | 1/1 | 33533 | Thomas/ CV Surgeon | 260 | 1000 | | |
| 6 | 1/1 | 33533/ AA | Jacobs/ Anesthesia | 260 | 5300 | | |
| 7 | 1/1 | 27130 | Buss/ Orthopedics | 727 | 2300 | HIPREP | **\*X** |
| 8 | 1/1 | 33533 | Smith/ FP | 997 | 120 | | |
| 9 | 1/1 | 93682/ AA | Jacobs/ Anesthesia | 260 | 1000 | | |
| 10 | 1/1 | 92982 | Breaker/ Cardiology | 260 | 1500 | | |

Fig. 2H

| PEG-Anchor Procedure Code | DESCRIPTION | PEG-Anchor Category | Description |
|---|---|---|---|
| 33510 | CAB VEIN ONLY 1 C VEN GRF | CABG | CORONARY ARTERY BYPASS GRAFT |
| 33516 | CAB VEIN ONLY 6/> C VEN GRFS | CABG | CORONARY ARTERY BYPASS GRAFT |
| 33533 | CAB W/ARTL GRF 1 ARTL GRF | CABG | CORONARY ARTERY BYPASS GRAFT |
| 33534 | CAB W/ARTL GRF 2 C ARTL GRFS | CABG | CORONARY ARTERY BYPASS GRAFT |
| S2205 | MIN INVASV DIR CAB SURG; ART GFT 1 COR ART GFT | CABG | CORONARY ARTERY BYPASS GRAFT |
| S2206 | MIN INVASV DIR CAB SURG; ART GFT 2 COR ART GFT | CABG | CORONARY ARTERY BYPASS GRAFT |
| 33207 | INSJ/RPLCMT PRM PM W/TRANSVNS ELTRD VENTR | IMPPAC | IMPLANTABLE DEVICE PACEMAKER |
| 33208 | INSJ/RPLCMT PRM PM W/TRANSVNS ELTRD ATR&VENTR | IMPPAC | IMPLANTABLE DEVICE PACEMAKER |
| 92975 | THROMBOLSS C INTRAC NFS SLCTV C ANGRPH | TXCAT1 | CORONARY ARTERY CATHETERIZATION (THERAPEUTIC) |
| 92982 | PRQ TRLUML C BALO ANGIOP 1 VSL | TXCAT1 | CORONARY ARTERY CATHETERIZATION (THERAPEUTIC) |
| 27130 | HIP REPLACEMENT LEFT | HIPREP | HIP REPLACEMENT OF THE LEFT HIP |

Fig. 3A

| PEG Anchor Category | Description | CLOSE Time Period | | FURTHER Time Period | |
|---|---|---|---|---|---|
| | | Pre-Window | Post-Window | Pre-Window | Post-Window |
| CABG | CORONARY ARTERY BYPASS GRAFT | 14 | 42 | 180 | 365 |
| CLVAL | CLOSED VALVE REPAIR | 14 | 42 | 180 | 365 |
| IMPDEF | IMPLANTABLE DEVICE DEFIBRILLATOR | 14 | 42 | 180 | 365 |
| IMPPAC | IMPLANTABLE DEVICE PACEMAKER | 14 | 42 | 180 | 365 |
| OPVAL | SURGICAL VALVE REPAIR | 14 | 42 | 180 | 365 |
| TXCAT1 | CORONARY ARTERY CATHETERIZATION (THERAPEUTIC) | 14 | 42 | 180 | 365 |
| TXCAT2 | CORONARY ARTERY CATHETERIZATION W/ NON-DRUG STENT | 14 | 42 | 180 | 365 |
| TXCAT3 | CORONARY ARTERY CATHETERIZATION W/ - DRUG STENT | 14 | 42 | 180 | 365 |
| TXEP | INVASIVE THERAPEUTIC (ABLATION) ELECTROPHYSIOLOGY | 14 | 42 | 180 | 365 |

Fig. 3B

| Procedure Code Modifier | Description |
|---|---|
| -21 | Prolonged Evaluation and Management Services |
| -22 | Unusual Procedural Services |
| -23 | Unusual Anesthesia |
| -82 | Assistant Surgeon (when qualified resident surgeon not available) |
| -90 | Reference (Outside) Laboratory |
| -91 | Repeat Clinical Diagnostic Laboratory Test |

Fig. 4

| PEG Anchor Category | Description | Specialty Ranking | Provider Code | Provider Type |
|---|---|---|---|---|
| CABG | CORONARY ARTERY BYPASS GRAFT | 1 | 1231 | CV SURGEON |
| CABG | CORONARY ARTERY BYPASS GRAFT | 2 | 1312 | VASCULAR |
| CABG | CORONARY ARTERY BYPASS GRAFT | 2 | 1521 | THORACIC |
| CABG | CORONARY ARTERY BYPASS GRAFT | 3 | 1311 | GENERAL SURGEON |

Fig. 5

| PEG Anchor Category | Description | ETG | Description | PPC | Description |
|---|---|---|---|---|---|
| CABG | CORONARY ARTERY BYPASS GRAFT | 251 | Coronary artery disease, with AMI, with coronary artery bypass graft | 8 | CARDIOLOGY |
| CABG | CORONARY ARTERY BYPASS GRAFT | 252 | Coronary artery disease, with AMI or acquired defect, with valvular procedure | 8 | CARDIOLOGY |
| CABG | CORONARY ARTERY BYPASS GRAFT | 253 | Coronary artery disease, with AMI, with angioplasty | 8 | CARDIOLOGY |
| CABG | CORONARY ARTERY BYPASS GRAFT | 254 | Coronary artery disease, with AMI, with arrhythmia, with pacemaker implant | 8 | CARDIOLOGY |
| CABG | CORONARY ARTERY BYPASS GRAFT | 255 | Coronary artery disease, with AMI, with cardiac catheterization | 8 | CARDIOLOGY |
| CABG | CORONARY ARTERY BYPASS GRAFT | 256 | Coronary artery disease, with AMI, anterior wall, with complication | 8 | CARDIOLOGY |
| CABG | CORONARY ARTERY BYPASS GRAFT | 257 | Coronary artery disease, with AMI, anterior wall, w/o complication | 8 | CARDIOLOGY |
| CABG | CORONARY ARTERY BYPASS GRAFT | 258 | Coronary artery disease, with AMI, inferior wall, with complication | 8 | CARDIOLOGY |
| CABG | CORONARY ARTERY BYPASS GRAFT | 259 | Coronary artery disease, with AMI, inferior wall, w/o complication | 8 | CARDIOLOGY |
| CABG | CORONARY ARTERY BYPASS GRAFT | 260 | Coronary artery disease, w/o AMI, with coronary artery bypass graft | 8 | CARDIOLOGY |
| CABG | CORONARY ARTERY BYPASS GRAFT | 268 | Congestive Heart Failure, w/o comorbidity | 8 | CARDIOLOGY |

Fig. 6

| PEG Anchor Category | Description | Precedence 1 | Precedence 2 |
|---|---|---|---|
| CABG | CORONARY ARTERY BYPASS GRAFT | 1 | 2 |
| CLVAL | CLOSED VALVE REPAIR | 2 | 1 |
| IMPDEF | IMPLANTABLE DEVICE DEFIBRILLATOR | 2 | 5 |
| IMPPAC | IMPLANTABLE DEVICE PACEMAKER | 2 | 7 |
| OPVAL | SURGICAL VALVE REPAIR | 1 | 1 |
| TXCAT1 | CORONARY ARTERY CATHETERIZATION (THERAPEUTIC) | 2 | 4 |
| TXCAT2 | CORONARY ARTERY CATHETERIZATION W/ NON-DRUG STENT | 2 | 3 |
| TXCAT3 | CORONARY ARTERY CATHETERIZATION W/ DRUG STENT | 2 | 2 |
| TXEP | INVASIVE THERAPEUTIC (ABLATION) ELECTROPHYSIOLOGY | 2 | 6 |

Fig. 7

| PEG Anchor Category | Description | Target Category | Description |
|---|---|---|---|
| CABG | CORONARY ARTERY BYPASS GRAFT | CHOLAB | LAB TESTS TO EVALUATE ELEVATED CHOLESTEROL |
| CABG | CORONARY ARTERY BYPASS GRAFT | CHOMED | MEDICINE FOR TREATING CHOLESTEROL |
| CABG | CORONARY ARTERY BYPASS GRAFT | DXCATH | CORONARY ARTERY CATHETERIZATION (DIAGNOSTIC) |
| CABG | CORONARY ARTERY BYPASS GRAFT | ECHO | ECHOCARDIOGRAPHY |
| CABG | CORONARY ARTERY BYPASS GRAFT | EKG | EKG |
| CABG | CORONARY ARTERY BYPASS GRAFT | ETT | EXERCISE STRESS TEST |

Fig. 8

| Target Category | Description | Target Procedure Code | Description |
|---|---|---|---|
| CHOLAB | LAB TESTS TO EVALUATE ELEVATED CHOLESTEROL | 80061 | LIPID PANEL |
| CHOLAB | LAB TESTS TO EVALUATE ELEVATED CHOLESTEROL | 82465 | METABOLIC PANEL |
| CHOLAB | LAB TESTS TO EVALUATE ELEVATED CHOLESTEROL | 83721 | LIPOPROTEIN DIR MEAS LDL CHOLESTEROL |
| CHOMED | MEDICINE FOR TREATING CHOLESTEROL | 0006F | STATIN THERAPY PRESCRIBED |
| CHOMED | MEDICINE FOR TREATING CHOLESTEROL | 4002F | STATIN THER PRESCRIBED |
| DXCATH | CORONARY ARTERY CATHETERIZATION (DIAGNOSTIC) | 93508 | CATH PLMT C ART CONDUIT&/VEN C BPG F/C ANGRPH |
| DXCATH | CORONARY ARTERY CATHETERIZATION (DIAGNOSTIC) | 93532 | CMBN R HRT T-SEPTAL L HRT CATHJ NTC SEPTUM CGEN |
| DXCATH | CORONARY ARTERY CATHETERIZATION (DIAGNOSTIC) | 93533 | CMBN R HRT T-SEPTAL L HRT CATHJ SEPTAL OPNG CGEN |

Fig. 9

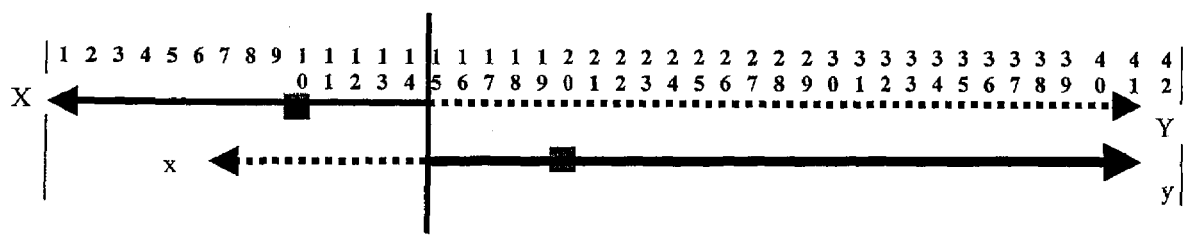
Legend:
| Day 15: Truncation date for PEG 1 and PEG 2 when PEG anchor procedure 1 was encountered on Day 10 and PEG anchor procedure 2 was encountered on Day 20.
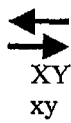 Claims identified during this period are for PEG 1
Claims identified during this period are for PEG 2
XY  Pre- and post-window periods for PEG 1
xy  Pre- and post-window periods for PEG 2
Fig. 10

SYSTEM AND METHOD FOR GROUPING CLAIM RECORDS ASSOCIATED WITH A PROCEDURE

This application is a continuation of U.S. patent application Ser. No. 11/759,616, filed Jun. 7, 2007, now issued as Pat. No. 7,801,749 on Sep. 21, 2010, the content of which is hereby incorporated in its entirety by reference.

FIELD OF THE INVENTION

The present invention relates to a system and method for grouping claim records associated with a procedure, and more specifically to a system and method for grouping medical claim records based upon the claim records' relationship with one or more medical procedures.

BACKGROUND

In the analysis of medical claim records, it may be helpful to group the records in various ways to enable meaningful analysis of the records for various purposes. Grouping of medical claim data may be accomplished using a number of methodologies, for example, by grouping claim records based upon diagnosis and/or procedure codes (such as ICD (International Classification of Disease) codes and/or CPT (Current Procedure Terminology) codes promulgated by the American Medical Association). Additional grouping methodologies are described in such patents as U.S. Pat. Nos. 5,557,514, 5,835,897, and 5,970,463. These and other existing methodologies support the analysis of medical claims data by various units of analysis, including populations or members, episodes of care or diseases/conditions, and inpatient admissions.

However, the existing methodologies are not as helpful in assessing, for example, the relative performance of surgical specialists and other therapeutic procedures. The groupings created using the known methodologies often include in their group a wide range of other services in addition to the surgical or other therapeutic procedure in question. The wide range of services often includes services that the surgical specialist does not oversee, control or perform. One possible solution is to limit claim groups to services that occur on the same day as the procedure in question. However, such a unit is often too narrowly focused and may exclude meaningful treatment decisions and outcomes before and after the procedure.

SUMMARY

In view of the drawbacks of the existing medical claim grouping methodologies discussed above, the present invention relates to an improved system and method for grouping medical records by implementing a multi-level analysis of the records. The level of analysis for each record is determined based upon the time proximity of each record to the defining medical procedure or service to be analyzed.

The system and method may be implemented to group medical claim records associated with an identified health-related procedure, such as a surgical or other therapeutic procedure to capture the sequence of care surrounding the identified procedure and thereby enable improved assessment of the cost and utilization associated with the identified procedure. In one embodiment, an anchor procedure is identified from medical claim records associated, for example, with a specific patient, health plan member, group of patients or health plan members, or specific healthcare provider or group of providers. The anchor procedure is a major therapeutic procedure performed by a clinician on a patient and may be identified via procedure or revenue codes on one or more claims. The anchor procedure is associated with one or more diagnostic and/or procedure codes (or other grouping category, such as episode treatment group codes) and a predefined time window. There may be multiple anchor procedures.

Once an anchor procedure claim record is identified, the remaining claim records are processed to determine whether any of the records should be grouped with the anchor procedure into a procedure episode group or PEG. In order to form a PEG of claim records, the date of service for each claim record is identified to determine whether the each claim record falls within a time window, and, if so, where within the time window (using the date of service associated with each claim record). The claim records falling within the window then are assessed to determine whether each claim record relates to the anchor procedure (for example, by determining whether the diagnostic, procedure, or episode treatment group coding of each claim record is associated with the anchor procedure). The requisite relationship level between the claim records and the anchor procedure depends upon the position of the claim records within the time window.

In particular, one or more different levels of analysis are associated with different portions or sub-windows within the time window. For claim records falling within the time window, each claim record date of service determines where within the window the record falls, and this position is used to determine the associated level of relationship between the claim record and the anchor procedure or the associated level of analysis of the claim record that is required before adding the record to the PEG. Claim records having no relation to the anchor procedure and/or not falling within the time window are excluded from the PEG (and may be assessed for inclusion into other PEGs). Additionally, claim records not meeting the requirements associated with the part of the time window in which they fall based on their date of service are also excluded from the PEG.

An exemplary method of grouping claim records includes identifying an anchor procedure having an associated time window; collecting claim records to be analyzed; identifying claim records falling within the associated time window using the date of service associated with each claim record; assessing the identified claim records falling within a first portion of the time window to determine whether the identified claim records have a first level of relationship with the anchor procedure; assessing the identified claim records falling within a second portion of the time window to determine whether the claim records have a second level of relationship with the anchor procedure; and grouping the identified claim records respectively having the first and second level of relationship with the anchor procedure into a procedure episode group.

A system for grouping claim data associated with a medical procedure may include a database for storing claim data and a processor for identifying an anchor procedure from a set of claims and assigning an anchor category to the identified anchor procedure. The assigned anchor category is defined as an aggregation of clinically similar therapeutic procedures with an associated time window. The processor identifies claim data falling within the anchor category time window and assesses the identified claim data to determine the level of relationship between the identified claim data and the anchor category. The assessment of the claim data varies based upon the position of the claim data within the time window as determined by the date of service associated with the claim data. In one embodiment, claim data that is temporally close to the anchor procedure and related (clinically similar) to the anchor category is grouped into a grouping unit such as procedure episode group. Claim data that is temporally further removed from the anchor procedure must not only be related to the anchor category, but must also have a procedure code that is clinically associated with the anchor category in order to be included in the grouping unit.

These and other features and advantages of the present invention will become apparent to those skilled in the art from the following detailed description, wherein it is shown and described illustrative implementations of the invention, including best modes contemplated for carrying out the invention. As it will be realized, the invention is capable of modifications in various obvious aspects, all without departing from the spirit and scope of the present invention. Accordingly, the drawings and detailed description are to be regarded as illustrative in nature and not restrictive.

DESCRIPTION OF THE DRAWINGS

FIGS. 2A-2H depict an exemplary series of claims for identifying anchor procedure claims.

FIG. 3A an exemplary mapping of anchor procedure claims to procedure episode group anchor categories.

FIG. 3B provides a table depicting exemplary time windows associated with various procedure episode group anchor categories.

FIG. 4 provides a table of exemplary procedure code modifiers that may subject a claim to elimination.

FIG. 5 provides a table of exemplary provider specialty codes associated with the anchor category "CABG."

FIG. 6 provides a table of an exemplary subset of the anchor category "CABG" having associated episode treatment groups under Major Practice Category 8.

FIG. 7 provides an exemplary hierarchy and priority assignment of cardiovascular procedure episode group anchor categories.

FIG. 8 depicts an exemplary mapping between procedure episode group anchor categories and target categories.

FIG. 9 provides an exemplary chart showing mapping between target categories and target procedures for cardiovascular surgeries.

FIG. 10 illustrates an example for a pre-window and post-window search during a close time period.

DETAILED DESCRIPTION

A methodology for grouping claim records associated with a procedure will now be described in detail with reference to the accompanying drawings.

Figure 1:
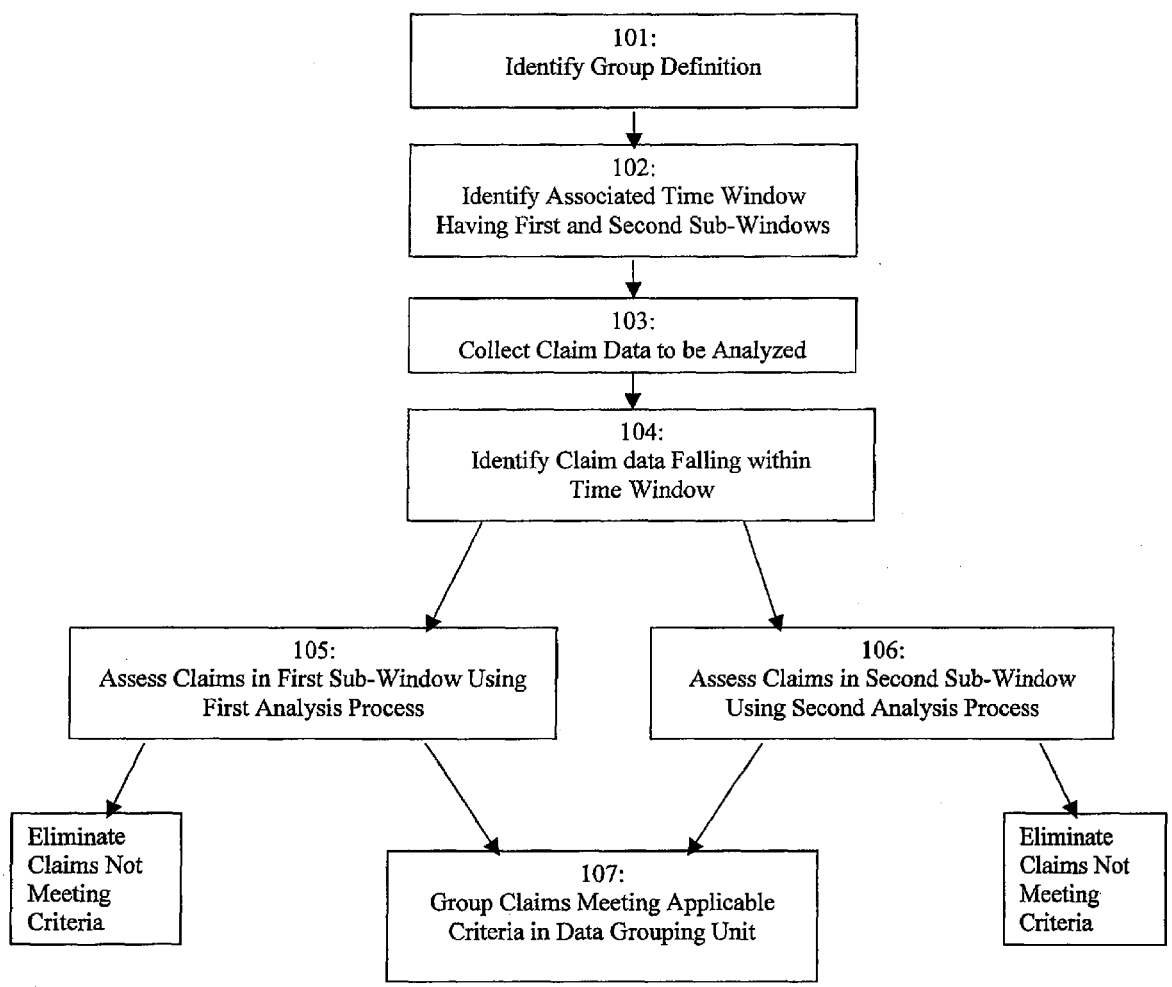
FIG. 1 provides a flowchart of a method for grouping claim records associated with a procedure by creating one or more claim record grouping units, each having one or more associated claim records.

With reference to FIG. 1, a method for grouping claim data into one or more groups of health-related claim data may be performed as follows:

101—Identify a defining subject matter for the data group ("group definition"), for example, a type of service, procedure or treatment; an anchor procedure (as described in detail below); or one or more specific diagnostic codes, procedure codes, and/or episode treatment group codes. Each group definition may comprise one or more procedures, categories, codes, etc. A plurality of different group definitions may be stored.

A group definition may, for example, be defined using one or more procedure codes, such as CPT codes, HCFA Common Procedure Coding System codes (coding system promulgated by the CMS and used to bill federal health entitlement programs), or National Uniform Billing Committee Revenue codes; anchor procedures and anchor categories (described below in detail); episode treatment groups (ETGs), wherein ETGs combine all routinely collected inpatient, outpatient, and ancillary claims data into mutually exclusive and exhaustive categories to provide a unit of analysis for the creation of provider profiling, demand analysis, and disease management strategies; diagnostic codes, such as ICD-9 codes; or any other desired group definition.

102—Identify a time window W having multiple sub-parts, such as A and B in Time Window Example 1 below, that is associated with the group definition. For example, each stored group definition may have an associated pre-defined time window period. The dates for the window for each group may be determined using the pre-defined window period and a date associated with the group, such as the date on which the anchor procedure for the group is performed.

103—Collect all claim data to be analyzed, such as all claim data associated with a particular patient or health plan member, a group of patients or health plan members, or a particular provider or group of providers. In some implementations, the claim data to be grouped may have been previously analyzed or grouped, for example, into episode treatment groups as described in U.S. Pat. No. 5,835,897, issued on Nov. 10, 1998, and entitled "Computer-Implemented Method for Profiling Medical Claims," which is incorporated herein by reference in its entirety.

104—Using the date of service associated with the selected claim data, determine whether the selected claim data falls within the time window W, and if so, in which part (A or B) of the window W. Claim data falling outside of the time window W is eliminated from further processing (but may be assessed for inclusion in other groups).

105—Assess the selected claim records falling within a first sub-window (e.g., A in Example 1 below) within the multi-part window using a first analysis process to determine the level or extent of relation to the group definition. Eliminate claim data that does not meet the assessment criteria.

106—Assess the selected claim records falling within second sub-window (e.g., B in Example 1 below) within the multi-part window using a second analysis process to determine the level or extent of relation to the group definition. Eliminate claim data that does not meet the assessment criteria.

107—Integrate or group all claim data meeting the selection criteria into a data grouping unit, for example, a procedure episode group as described below.

TIME WINDOW EXAMPLE 1

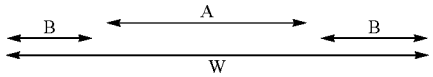

Notably, the time window W shown above is provided for illustrative purposes and is not intended to limit the number and/or configuration of sub-windows within window W. It is contemplated that various numbers and configurations of sub-windows may be implemented, wherein the position of claim data (as determined by the date of service associated with the claim data) within the window, i.e., the particular sub-window in which the claim data falls, determines the type or level of analysis that is used to determine whether the claim data should be grouped into the data grouping unit.

Figure 1A:
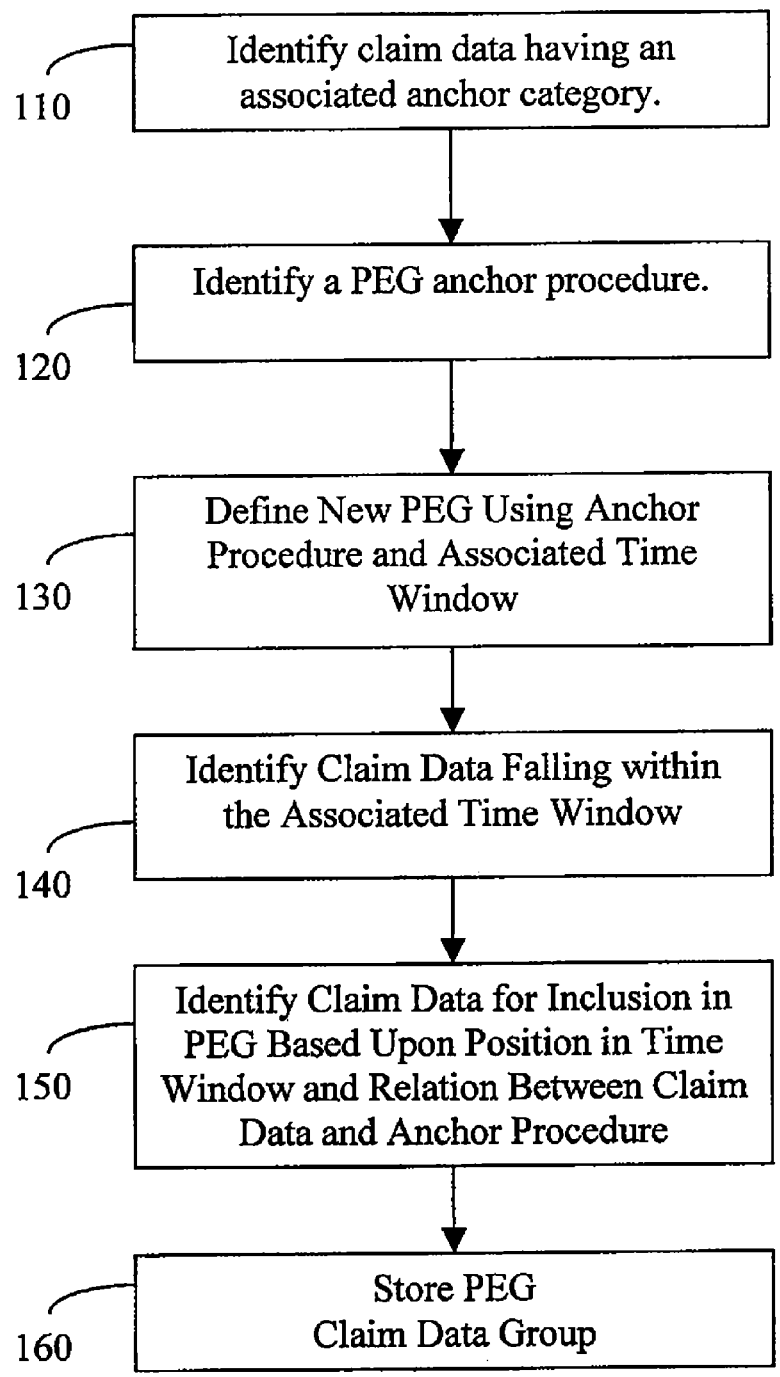
FIG. 1A provides an alternative flowchart of a method for grouping claim records associated with a procedure by creating one or more procedure episode groups, each having one or more associated claim records.

FIG. 1A illustrates an exemplary method for grouping claim records or claim data into a procedure episode group (PEG). Each PEG may include (1) all workup and conservative care associated with a specific therapeutic procedure, such as a surgical procedure, that occurs before a therapeutic procedure (e.g., all claim records relating to physical therapy undergone prior to surgical intervention for back pain), (2) the therapeutic procedure itself, and (3) the associated follow-up after the procedure, including any re-admission and repeated procedures.

With reference to FIG. 1A, according to an exemplary PEG grouping methodology, medical claim records, such as records for a specific patient or provider, are analyzed to determine whether a new PEG should be created. Each record in a set of claim records is assessed to identify whether the record content (e.g., the procedure code) corresponds to one or more predefined anchor categories. Each anchor category represents an aggregation of clinically similar procedures. Each anchor category also has an associated time window and may also include one or more associated diagnostic, procedure, and or prescription codes; episode treatment groups (ETGs); target categories; and/or target procedures. An exemplary list of anchor categories and associated ETGs is provided in FIG. 6. Target categories and procedures are provided in FIGS. 8 and 9 respectively.

In 110, claim records that have one or more associated anchor categories are assigned to the appropriate anchor categories. Claim records that do not have an associated anchor category are eliminated from further consideration as possible anchor procedures that may define a new PEG.

In 120, the claim records having an assigned anchor category are assessed to determine whether they qualify as an anchor procedure for a new PEG. An anchor procedure may be defined as a major therapeutic procedure such as orthopedic surgery, back surgery, cardiac surgery, abdominal surgery, skin and plastic surgery, eye surgery, gynecologic surgery, urologic surgery, ear-nose-throat surgery, or other surgical or other therapeutic procedure. Anchor procedures generally are significant procedures that are intended to treat a condition or disease, as contrasted with diagnostic procedures that are intended to diagnose a condition or disease. Notably, the PEG grouping methodology is not limited to identifying anchor procedures falling into those described above, and that additional therapeutic procedures may be used as an anchor procedure. For example, a hospital admission may be an anchor procedure associated with a PEG.

Thus, in 120, one or more anchor procedures are identified from the set of claim data created in 110 based upon the content of each record and its predefined priority with respect to other claim records in the same anchor category. An exemplary process for identifying anchor procedures is provided below with reference to FIGS. 2A-2H.

In 130, using the identified anchor procedures, a new PEG is created for each identified anchor procedure. The PEG is defined using the anchor category associated with the anchor procedure and has an associated time window that may be predefined in association with the particular PEG anchor category. In some cases multiple closely related anchor procedures may be included in the same PEG (as illustrated in the example provide in FIG. 2H).

In 140, each record in the initial set of claim records is assessed to determine whether the service represented by the claim record was performed within the predefined time window associated with any of the PEGs created in 130 or any other existing PEGs.

Figure 3C:
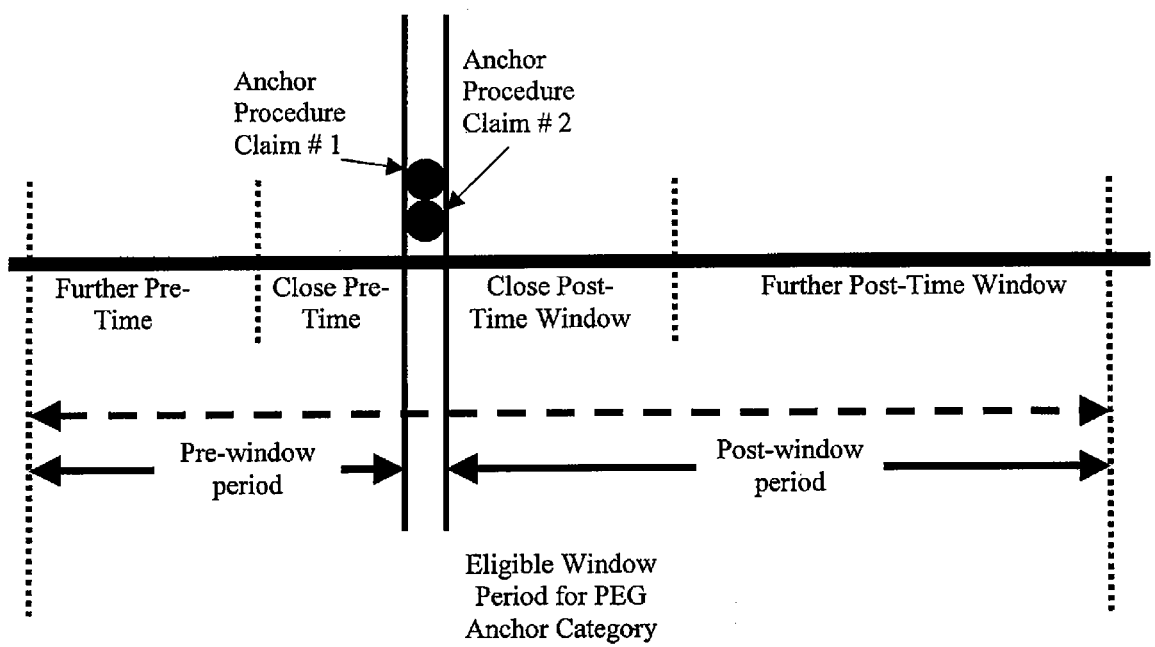
FIG. 3C is a graphical depiction of an exemplary timeline associated with an anchor category.
Figure 3D:
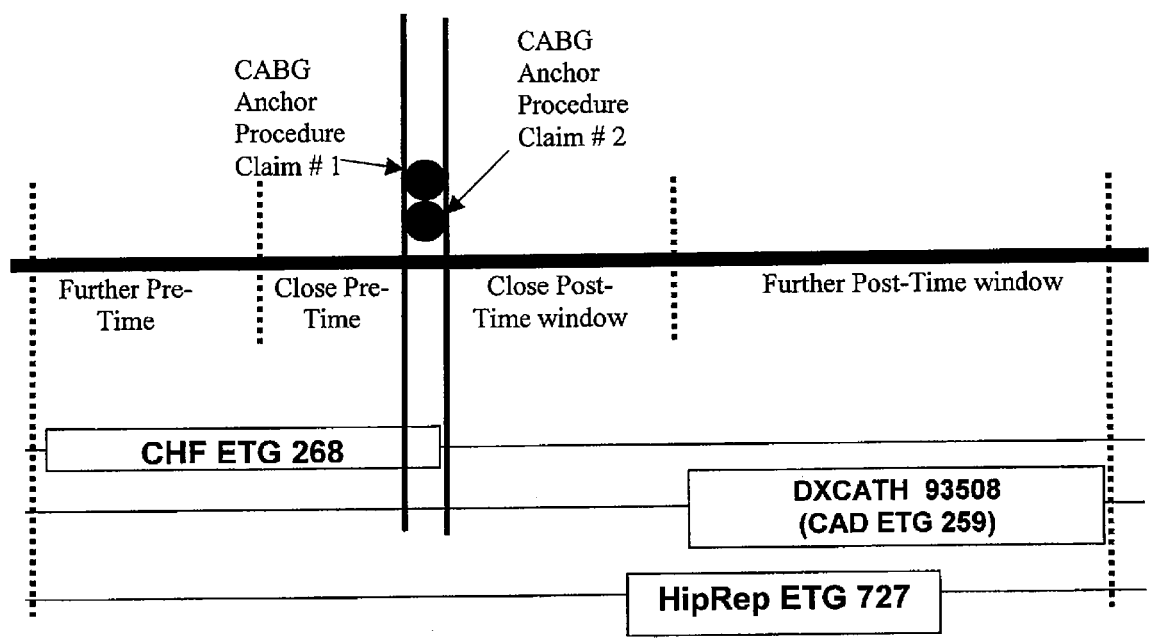
FIG. 3D is a graphical depiction of an episode treatment group considered for inclusion into a procedure episode group having "coronary artery bypass graft" (CABG) as the anchor category.

In 150, claim records falling within the time window for a selected PEG are assessed to determine whether the claim record should be included in the PEG based both upon where the service date falls within the time window and the contents of the claim record. For example, with reference to Example 2 below, a time window W associated with a PEG may comprise a first close time sub-window A and a second further time sub-window B, each centered around the anchor procedure for the PEG. In this example, both sub-windows A and B incorporate time periods before and after the anchor procedure. Another exemplary full time window having a first and second sub-window associated with a two CABG anchor procedures is illustrated in FIG. 3D and described in further detail below. In alternative embodiments, the full window may comprise any number of sub-windows to enable multiple different types or levels of analyses of claim records falling within each sub-window as described below.

TIME WINDOW EXAMPLE 2

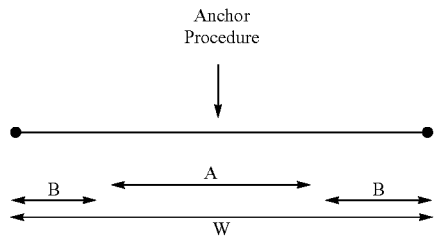

In 150, claim records having a date falling within the full time window W are further assessed to determine whether each record has a date falling within the first sub-window A or the second sub-window B. Claim records that fall within the first sub-window A are assessed to determine whether they generally relate to the anchor procedure, for example, based upon the type or category of service, for example, as indicated by the diagnosis code, procedure code, or ETG codes associated with each record and the definition of the anchor category of the PEG (see FIG. 6). Claim records having a date within the first sub-window A and having a relationship with the anchor procedure are included in the PEG. Claim records falling within the first sub-window that have no relationship with the anchor category of the PEG are eliminated (and may be evaluated for inclusion in other PEGs).

Claim records having a date falling within the second sub-window B are processed similarly to the claim records in the first sub-window A as described above to determine whether the records are related to the anchor category of the PEG. Those records within the second sub-window B having no relation to the anchor category of the PEG are eliminated. However, because the second sub-window B is further removed temporally from the anchor procedure(s) of the PEG, further analysis of the related records is used to insure that the further-removed records should be included in the PEG. In one embodiment, this additional analysis involves an assessment of the records to determine whether the procedure or treatment in the record is associated with at least one target category or target procedure associated with the anchor category of the PEG (see FIGS. 8 and 9). If so, the claim records are grouped into the PEG, and, if not, they are excluded (and can be evaluated for possible inclusion in other PEGs). Additional and/or alternative analyses to confirm the relationship between the claim records in the second sub-window B and the anchor category of the PEG may be used.

In 160, the claim records identified in steps 140 and 150 that are grouped into the PEG are stored.

The methods illustrated in FIGS. 1 and 1A provide for grouping of claim records using a multi-level analysis of claim records based upon both the date of service and the nature or type of service represented by each record. Records having a date in closer proximity to the anchor procedure of the PEG may undergo a different analysis than records further removed temporally from the anchor procedure. While the embodiment described above relates to the use of two sub-windows (A and B), with records in the second sub-window being subjected to additional analysis to confirm their relation to the anchor category of the PEG, multiple sub-windows and multiple different analysis are contemplated.

In one embodiment, claim data is assigned or grouped to ETG categories prior to performance of the grouping methodology described in FIG. 1A. Anchor procedures used as group definitions for PEGs may be identified based on the procedure's episode treatment group (ETG) code, claim procedure code, and/or provider type. In some configurations, where the ETG code assigned to a claim indicates a value that is unrelated to the anchor category associated with the claim, the procedure associated with claim will be eliminated from consideration as an anchor procedure.

Where a procedure code associated with a claim includes a procedure code modifier that reflects a provider status that is ancillary, e.g., anesthesia or assistant surgeon, the procedure associated with the claim may be eliminated from consideration as an anchor procedure. FIG. 4 provides an exemplary table of procedure code modifiers that may be utilized to eliminate a claim from consideration as an anchor procedure.

In addition, in some implementations, a provider specialty code in the claim data that reflects the clinical specialty associated with the claim data may be required in order for the claim's procedure to be considered the anchor procedure. FIG. 5 provides a table of provider specialty codes associated with the anchor category CABG (coronary artery bypass graft).

In some instances a multi-claim anchor procedure may be identified when multiple claims occur on the same date of service that satisfy the anchor procedure requirements, described further below in relation to FIGS. 2A-2G.

An exemplary procedure for identifying an anchor procedure that can be used to define a PEG will now be described with reference to FIGS. 2A-2G. FIG. 2A illustrates a claim data stream having claims #1 to #10, each performed on the same date, January 1 (1/1). The claims in the claim data stream are analyzed based on the claim procedure code, procedure code modifier and provider specialty and compared to, for example a mapping of anchor procedures to anchor categories depicted in FIG. 3A, and labeled (see PEG Anchor Category column in FIG. 2B) with a potential anchor category, where applicable. Claims not having a potential anchor category (italicized claim lines in FIG. 2B) are subsequently removed (FIG. 2C). In FIG. 2B, claim 1 is italicized and slated for elimination as an anchor procedure for two reasons, first because the procedure code has a procedure code modifier—91, which indicates that the procedure is a repeat clinical diagnostic laboratory test (see FIG. 4), and second because the provider has an "ancillary" specialty designation and is not a clinician. Claim 2 is slated for elimination because the procedure code does not map to any anchor category. Claim 6 is slated for elimination because the procedure code modifier "AA" is subject to elimination (AA, anesthesia, assistant surgeon). Claim 9 is also slated for elimination because of its modifier.

In FIG. 2C, the claims having an assigned anchor category are grouped and analyzed to determine whether ETG categories are present that do not map in the anchor category-to-ETG category clinical rules. In FIG. 2C, claim 8 is slated for removal removed because it groups to an ETG category that CABG does not map to in the anchor category-to-ETG category clinical rules (see FIG. 6, ETG 997 does not appear in the "PEG Anchor Category to ETG category" chart).

Claims that do not contain a valid ETG code (or are assigned an ETG code indicating that there is an error in the claim data) may be excluded from consideration as a potential anchor procedure for a new PEG. However, these claims may be assessed later in the process, for example, assessed as a possible target procedure, to determine whether they should be included in an existing PEG.

In FIG. 2D, the claims with PEG anchor categories are filtered based on the PEG practice category (PPC) each anchor category is associated with. A PPC is a grouping of anchor categories that relate to a particular body system. FIG. 6 provides an exemplary table of a subset of the anchor category CABG having associated ETGs under PPC 8, for cardiology. Claim 10 having the anchor category TXCAT1 is also grouped under PPC 8, for cardiology. Claims having a PPC that is different from the identified PPC, e.g., PPC 8, are filtered out. Accordingly, claim 7 is slated for removal because it is associated with the orthopedic PPC, while the other claims are in the cardiovascular PPC. Claim 7 will be assessed with other orthopedic claims and grouped into an appropriate PEG.

In FIG. 2E, where there is more than one PEG-Anchor Category remaining in the PPC, PEG anchor categories will be compared based on assigned precedence rankings. A precedence 1 number is assigned to each anchor category, and a precedence 2 number is assigned to PEG anchor categories within a PPC that have the same precedence 1 value. FIG. 7 is an exemplary chart showing the precedence value assignments of cardiovascular PEG anchor categories. When two or more PEG anchor categories within the same PPC are identified for claims having the same date of service, the precedence 1 numbers for the PEG anchor categories are compared. The claim or claims with the anchor category having the lowest precedence 1 number will become the anchor category on which grouping activities take place. However, if the precedence 1 numbers for competing PEG anchor categories are equal, the precedence 2 numbers for each anchor category are compared with the other(s). The claim or claims with the anchor category having the lowest precedence 2 number will become the anchor category on which grouping activities will take place. Accordingly, in FIG. 2E, claim 10 is removed from consideration as because it maps to the TXCAT1 anchor category, which has a precedence 1 score of 2, which is less significant than the CABG precedence 1 score of 1 (see FIG. 6).

In addition to identifying the appropriate anchor category, according to certain implementations, the responsible provider for the PEG is identified. In FIG. 2F, providers with the highest specialty ranking only are identified and retained. In this example, no claims are eliminated between FIGS. 3F and 3G because all of providers are of the same specialty, "CV Surgeon." If either Dr. Jones or Dr. Thomas had been a General Surgeon, they, and their claims, would have "lost" to the CV Surgeon specialty provider based on the provider specialty ranking, and thus would have been eliminated (see FIG. 5).

In FIG. 2G, in order to identify the responsible provider when multiple providers have the same specialty ranking identifiers, the cost for the remaining claims are summed by provider. The provider with the highest cost will be identified as the responsible provider for the PEG. This provider's claims will represent the anchor procedure for this episode. According to FIG. 2G, claim 5 is eliminated, as Dr. Thomas' costs are $1000 and Dr. Jones' are $6700. Dr. Jones is identified as the responsible provider for the PEG. Claims 3 and 4 remain to serve as the anchor procedure for this episode. In some implementations where the costs attributed to each provider are the same, the provider with the lowest provider identification number value in the claim listing may serve as the responsible provider.

In FIG. 2H, the final anchor procedure identification for the claim set is provided by flagging the anchor procedure claims 3 and 4. A CABG PEG is defined using claims 3 and 4 as the anchor procedures. In addition, claim 7 is flagged as the anchor procedure for a hip replacement PEG.

After identifying the anchor procedure(s), the PEG grouping methodology creates one or more new PEGs and assigns an anchor category to each PEG based on the anchor procedure. FIG. 3A provides a table showing exemplary mapping between anchor procedure codes and PEG anchor categories for cardiovascular surgeries and a hip replacement surgery. The PEG anchor category for each PEG determines the type of claims that may be grouped into the PEG and the time window for grouping claim data into the PEG. FIG. 3B provides a table showing exemplary time windows associated with various anchor categories, and FIG. 3C is a graphical depiction of various time windows associated with an anchor category.

With reference to FIG. 3C, each PEG anchor category has an associated eligible time window, which may be the number of days between the start of a defined pre-window period and the end of a defined post-window period. The time window is searched to identify claim data having service dates within the window. The claim data to be analyzed may comprise, for example, all claim data associated with a particular patient or health plan member, a group of patients or health plan members, or a particular provider or group of providers. Claim data having an associated date of service falling within the time window is assessed for possible inclusion into the PEG as described below.

For claim data falling within the PEG time window, the analysis used to determine whether the claim should be included in the PEG depends upon where within the time window the claim occurred. For example, a claim having a date that is temporally proximate to the anchor procedure is treated differently than a claim having a date that is temporally more distant from the anchor procedure date.

FIG. 3B illustrates an exemplary table of pre- and post-window time frames for a close time period and a further time period for cardiovascular surgery PEG anchor categories. In the exemplary implementation of CABG in FIG. 3B, the default close time frame pre-window period is 14 days and the default post-window period is 42 days. For the further time frame, the default pre-window is 180 days and the default post-window period is 365 days. However, it will be understood that other pre- and post-window periods for the close and further time frames may be shorter or longer than the default time values.

For claims falling within the close period, if the claims are related to the PEG via the anchor category-to-ETG category relationship, the claims are included in the PEG. FIG. 6 shows an example of the ETG categories associated with the PEG anchor categories for cardiovascular surgeries. Using the anchor category initially assigned to the PEG, the PEG grouping methodology identifies claim lines that are assigned to ETG categories that are clinically related to the anchor category.

For claims falling within the further time period, inclusion in the PEG requires that the claims include target procedures related to the PEG via the anchor category-to-target category and/or target category-to-target procedure relationships. To determine whether a claim in the further time window is to be assigned to the PEG, the procedure code(s) (e.g., CPT codes) included in the claim are identified. If a procedure code in the claim corresponds to a target procedure associated with the anchor category, the claim is assigned to the PEG. The actual procedure codes associated with the claim, and not the ETG assignment associated with the claim, determine whether a claim falling only within the further time window is included in the episode. Thus, claims falling within the further time window are subjected to a more exacting analysis (i.e., requiring analysis of the procedure codes associated with the claim) than are claims in the close time window (for which the associated ETG is assessed) to determine whether they should be included in the PEG.

For example, using the anchor category initially assigned to the PEG, the PEG grouping methodology identifies individual claim lines that are identified as target procedures. Target procedures are diagnostic procedure codes that are clinically associated to a given PEG anchor category. The target procedures are aggregated into target categories, which are higher level aggregations of clinically similar target procedures. FIG. 8 is a chart that depicts an exemplary mapping between PEG anchor categories and target categories. FIG. 9 provides an exemplary chart showing mapping between target categories and target procedures for cardiovascular surgeries. Once a PEG anchor claim and all eligible claims during the close and further time periods are identified, the claims are aggregated to create a PEG.

FIG. 3D is a graphical depiction of episode treatment groups (ETGs) of claim data that may be considered for grouping into a PEG having CABG as the anchor category. In FIG. 3D, three ETGs are provided that fall within the time window for the PEG having CABG as the anchor category: CHF 268, CAD 259 (containing a claim representing procedure DXCATH 93508), and Hip Replacement 727.

CHF 268 falls at least partly in the closer pre-time window, encompasses at least one anchor procedure, and is an ETG that is clinically associated with the PEG anchor category (see FIG. 6). Claims assigned with ETG CHF 268 are therefore grouped into the CABG PEG of FIG. 3D.

The claim representing procedure DXCATH (diagnostic coronary artery catheterization) 93508 falls within the further post-time window in FIG. 3D. Therefore, claim DXCATH 93508 is examined to determine whether the procedure code(s) in the claim is a target procedure related to the CABG anchor category. FIGS. 8 and 9 provide charts depicting the relationship between the CABG anchor category and various target categories and the relation between the target categories and target procedures, respectively. According to FIG. 8, DXCATH is a target category associated with the CABG anchor category, and DXCATH is associated with the target procedure code 93052, from FIG. 9. Therefore, DXCATH 93508 is grouped into the PEG of FIG. 3D.

Also, one or more claims relating to a hip replacement procedure (having an ETG number of 727) fall in the post-time window of the PEG in FIG. 3D. As described above, each claim falling within the further time window is assessed to determine whether its procedure code(s) is a target procedure related to the CABG anchor category. In this instance, hip replacement procedures are not target categories related to the CABG anchor category (see FIGS. 8 and 9), and therefore these claims are not included in the PEG of FIG. 3D.

Various types of patient data may be used in the PEG grouping methodology. In some implementations, the data used as input for the PEG grouping methodology is pre-grouped into episodes, such as an ETG, as in FIG. 3D above. In some configurations, all or a part of the data from ETGs may be provided as input for the PEG grouping methodology. In alternative configurations, the claim data itself is the input for the PEG grouping process.

The various types of data that may be provided as input for the PEG grouping process include: a record ID, a unique identifier of the service line from a claim; a patient identifier, which may include a family ID and a patient ID; a procedure performed for a claim, which may be represented by procedure codes such as current procedure terminology (CPT) codes, e.g., CPT-4 codes, HCFA common procedure coding system (HCPCS) codes, e.g., HCPCS level 2 codes, ICD-9 codes, or NUBC (national uniform billing committee) revenue codes; a procedure code modifier for differentiating services provided by clinicians during treatment of a patient's condition or for characterizing the individuals who participated in performing a service, as well differentiation of laterality for certain procedures; a revenue code, which is similar to a procedure code in that it identifies the service performed; a provider identification number used to identify who performed the service; a provider type that represents the client-provided specialty of the provider who performed the service; an ETG number, which can represent a standard ETG or a super ETG; a sub-ETG for providing a finer level of specificity within some ETGs; a record type, e.g., the assigned ETG record type; an ancillary type, which allows differentiation of ancillary (record type='A') inpatient records from ancillary outpatient records; a first date of service and last date of service covered by the subject claim; an eligibility begin and end date, which are the first and last date on which the patient is eligible under the plan; and an amount paid and an amount charged for the claim.

Additional data may be provided for implementing the PEG grouping method and/or may be used to provide a more complete report when presenting the PEG. For example, additional data may include a patient's gender and age. In addition, other information such as an ordering provider identification number that identifies the provider who ordered the service; a cluster provider identification, where for ETG clusters created by a management or surgery record, is the provider ID from the management or surgery record that anchors (begins) the cluster, for clusters created by a confinement, the cluster provider identification is the responsible provider ID of the confinement; type of service represents the type of service performed for this claim as defined by the user; the ETG episode number to which the record grouped, which serves as a link between records in the ETG claim file and the records in the ETG summary file because all records in an ETG episode have the same episode number; the episode cluster number represents the building blocks of an ETG treatment episode; the episode type number, which normally indicates the completeness of an ETG episode, but can also indicate a record that is not capable of being grouped; and the date the claim was paid.

As described above with reference to FIGS. 2F and 2G, identification of the responsible provider may accompany identifying the anchor procedure and category. The responsible provider assignment methodology determines which provider has the highest degree of association with the PEG. Providers assigned to a PEG may need to meet certain criteria. For example, the provider may be required to be identified on a claim line having the same date of service as a claim line identified as the anchor procedure. In another example, the provider may not be categorized as providing ancillary services or as a provider that does not deliver the therapeutic procedure. For example, providers delivering anesthesia or that are categorized as an assistant surgeon (see FIG. 4) may be excluded from consideration as the responsible provider. In yet another example, the provider may be required to be of a provider type associated with a clinical specialty to which the PEG is assigned. According to some implementations, provider types found in claim data or in ETG files may need to be mapped to a set of provider specialty codes, which may be based on the IHCIS provider specialty level 4 codes or another pre-defined specialty code set.

The PEG grouping methodology my further account for instances when the pre- and/or post-windows overlap for two potential PEGs with PEG anchor categories that are associated with the same PPC. For example, PEG anchor categories CABG and TXCAT1 (described in FIG. 3B) both may be associated with the cardiovascular PPC and may overlap when the date of service for each procedure is different. When anchor procedures having different dates of service are identified for this circumstance, the PEG grouping methodology may truncate the pre- or post-window search, and thus truncate each episode, at the mid-point date of the overlap period between the anchor procedure dates. All of the claims before the truncation date will be gathered to the PEG that was encountered in the earlier time frame. All of the claims after the truncation date will be gathered to the PEG that was encountered in the later time frame.

The diagram of FIG. 10 provides a truncation example for a pre- and post-window search during the close time period. Anchor procedure 1 for PEG 1 is encountered on day 10, and anchor procedure 2 for PEG 2 is encountered on day 20. The truncation mid-point is day 15. Despite a post-window time period of 42 days, the post-window search for PEG 1 is truncated from day 11 through day 14, ending at the truncation point on day 15. Likewise the pre-window search for PEG 2 goes from day 19 through day 15, again ending at the truncation point, even though the pre-window time period is 14 days. The same principles may be applied for a pre- and post-window search during the further time period.

The PEG grouping methodology described above also may be configured to apply a flag to a PEG to indicate laterality of an anchor procedure, e.g., where one side of the patient's body is involved and the procedure can be performed on either the left or the right side of the anatomy. For example, laterality may be applicable for a knee replacement procedure. Laterality of an anchor procedure may be determined based on the procedure code modifier(s) found in the claim(s) that make up the anchor procedure.

PEGs may offer a more complete view of the resources used for therapeutic procedures, and therefore may provide a unit of analysis for creating financial knowledge for the therapeutic procedures assessed. In some configurations, the cost of inpatient-related PEGs may be risk-adjusted using a DRG grouper or other approach. Costs of outpatient-related PEGs may be risk-adjusted with an ERG model configured to predict PEG cost. According to some configurations, the PEG grouping methodology may drive an impact analysis in order to measure the financial impact of physicians primarily responsible for procedures.

PEGs may be utilized to identify a sequence of care for a therapeutic procedure, which can be compared to an exemplary sequence of care that is developed, for example, using past PEGs, literature, evidence based medicine, and/or expert opinions. A PEG that closely follows a model PEG or an exemplary sequence of care may be assigned a stronger rating compared to a PEG that correlates less closely to the model PEG, for example. In addition, quality markers may be developed for use in assessing the quality of the sequence of care prior and subsequent to a given anchor procedure. For example, a quality marker for the workup to a knee meniscectomy anchor procedure may be a knee MRI. A quality marker for conservative care prior to a lumbar laminectomy may include physical therapy and/or joint injections. Another quality indicator may be the time between the diagnosis of a condition and the therapeutic procedure to correct the condition. For example, if the time between diagnosis and the procedure is short, the surgeon may be considered too aggressive. Quality markers for post anchor procedure events may include physical therapy after orthopedic surgery, monitoring pacemakers after placement, readmissions, post-operative infections, removal of hardware, and anchor procedures that are repeated. According to certain implementations, the PEG grouping methodology may drive EBM, which may result in producing quality metrics related to the sequence of care.

The claim data grouping methodology described above may be implemented using various combinations of software and hardware as would be apparent to those of skill in the art and as desired by the user. For example, the present invention may be implemented in conjunction with a general purpose or dedicated network of computer components having processing and memory components.

From the above description and drawings, it will be understood by those of ordinary skill in the art that the particular implementations shown and described are for purposes of illustration only and are not intended to limit the scope of the present invention. Those of ordinary skill in the art will recognize that the present invention may be embodied in other specific forms without departing from its spirit or essential characteristics. References to details of particular implementations are not intended to limit the scope of the invention.

What is claimed is:

1. A computer-implemented method of grouping health-related claim records, comprising:
    storing in at least one electronic database:
        a plurality of health-related claim records for at least one patient; and
        a plurality of predefined anchor categories, each predefined anchor category including a plurality of clinically related procedures and at least one anchor procedure having an associated time window that is divided into a first sub-window portion and a second sub-window portion different from the first sub-window portion, wherein the first sub-window portion has an associated first claim analysis process and the second sub-window portion has an associated second claim analysis process; and
    using a computer processor to:
        identify an anchor procedure from the stored claim records having the associated time window;
        identify claim records falling within the associated time window using the date of service associated with each claim record;
        assess the identified claim records falling within the first sub-window portion of the time window using the first claim analysis process to determine whether the identified claim records have a first level of relationship with the anchor procedure in which the claim records generally relate to the predefined anchor category associated with the identified anchor procedure;
        assess the identified claim records falling within the second sub-window portion of the time window using the second claim analysis process to determine whether the identified claim records have a second level of relationship with the anchor procedure in which the claim records generally relate to the predefined anchor category associated with the identified anchor procedure, and in which the second claim analysis process further analyzes the claim records to confirm their relationship to the predefined anchor category;
        group the identified claim records respectively having the first and second level of relationship with the anchor procedure into a procedure episode group; and
        store the procedure episode group of claim records in the electronic database.

2. The method of claim 1, wherein the first sub-window portion of the associated time window for the anchor record is defined to be in temporally closer proximity to the anchor procedure than the second sub-window portion of the time window for the anchor record.

3. The method of claim 2, wherein determining the first level of relationship using the first claim analysis process comprises analyzing the claims in the first sub-window portion to determine whether the claim records are associated with ETG data having a predefined relationship to the anchor category.

4. The method of claim 3, wherein determining the second level of relationship using the second claim analysis process comprises further analyzing the claims in the second sub-window portion to determine whether the claim records are associated with procedure codes having a predefined relationship to the anchor category such that the second level of relationship requires a higher degree of relationship between the identified claim record and the anchor procedure than does the first level of relationship.

5. A computer-implemented system for grouping health-related claim records associated with a medical procedure, comprising:
    a database configured for storing:
        a plurality of health-related claim records for at least one patient; and
        a plurality of predefined anchor categories, each predefined anchor category including a plurality of clinically related procedures and at least one anchor procedure having an associated time window that is divided into a first sub-window portion and a second sub-window portion different from the first sub-window portion, wherein the first sub-window portion has an associated first claim analysis process and the second sub-window portion has an associated second claim analysis process;

a processor configured for:
- identifying an anchor procedure from the stored claim records having the associated time window;
- identifying claim records falling within the associated time window using the date of service associated with each claim record;
- assessing the identified claim records falling within the first sub-window portion of the time window using the first claim analysis process to determine whether the identified claim records have a first level of relationship with the anchor procedure in which the claim records generally relate to the predefined anchor category associated with the identified anchor procedure;
- assessing the identified claim records falling within the second sub-window portion of the time window using the second claim analysis process to determine whether the identified claim records have a second level of relationship with the anchor procedure in which the claim records generally relate to the predefined anchor category associated with the identified anchor procedure, and in which the second claim analysis process further analyzes the claim records to confirm their relationship to the predefined anchor category;
- grouping the identified claim records respectively having the first and second level of relationship with the anchor procedure into a procedure episode group; and
- storing the procedure episode group of claim records in the electronic database.

6. The system of claim 5, wherein the first sub-window portion of the associated time window for the anchor record is defined to be in temporally closer proximity to the anchor procedure than the second sub-window portion of the time window for the anchor record.

7. The system of claim 6, wherein determining the first level of relationship using the first claim analysis process comprises analyzing the claims in the first sub-window portion to determine whether the claim records are associated with ETG data having a predefined relationship to the anchor category.

8. The system of claim 7, wherein determining the second level of relationship using the second claim analysis process comprises further analyzing the claims in the second sub-window portion to determine whether the claim records are associated with procedure codes having a predefined relationship to the anchor category such that the second level of relationship requires a higher degree of relationship between the identified claim record and the anchor procedure than does the first level of relationship.

* * * * *